(12) United States Patent
Locklin

(10) Patent No.: US 8,968,421 B2
(45) Date of Patent: Mar. 3, 2015

(54) SYNTHESIS AND APPLICATION REACTIVE ANTIMICROBIAL COPOLYMERS FOR TEXTILE FIBERS

(71) Applicant: The University of Georgia Research Foundation, Inc., Athens, GA (US)

(72) Inventor: Jason J. Locklin, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/351,311

(22) PCT Filed: Oct. 12, 2012

(86) PCT No.: PCT/US2012/059887
§ 371 (c)(1),
(2) Date: Apr. 11, 2014

(87) PCT Pub. No.: WO2013/056004
PCT Pub. Date: Apr. 18, 2013

(65) Prior Publication Data
US 2014/0302302 A1    Oct. 9, 2014

Related U.S. Application Data

(60) Provisional application No. 61/547,120, filed on Oct. 14, 2011.

(51) Int. Cl.
*D06P 1/66* (2006.01)
*C08G 63/00* (2006.01)
*A01N 41/04* (2006.01)
*A01N 41/02* (2006.01)
*C08G 73/02* (2006.01)
*D06M 15/59* (2006.01)
*C08L 79/02* (2006.01)

(52) U.S. Cl.
CPC ............... *A01N 41/04* (2013.01); *A01N 41/02* (2013.01); *C08G 73/0226* (2013.01); *D06M 15/59* (2013.01); *C08L 79/02* (2013.01); *C08G 73/0206* (2013.01)
USPC ................... 8/115.66; 8/115.51; 525/412

(58) Field of Classification Search
USPC ................ 8/115.51, 115.66; 525/412
See application file for complete search history.

(56) References Cited

U.S. PATENT DOCUMENTS

| | | | | |
|---|---|---|---|---|
| 5,476,913 | A * | 12/1995 | Kourai et al. | 526/310 |
| 5,714,360 | A | 2/1998 | Swan et al. | |
| 6,872,241 | B2 | 3/2005 | Soane et al. | |
| 2004/0229975 | A1 | 11/2004 | Palumbo et al. | |
| 2010/0197888 | A1 | 8/2010 | Adib et al. | |

FOREIGN PATENT DOCUMENTS

WO    2010096444 A2    8/2010

OTHER PUBLICATIONS

STIC Search Report dated Jul. 17, 2014.*

* cited by examiner

*Primary Examiner* — Eisa Elhilo
(74) *Attorney, Agent, or Firm* — Thomas|Horstemeyer, LLP

(57) ABSTRACT

Polymer compositions, methods of making polymer compositions, structures (e.g., textile articles) having the polymer composition covalently bonded to the structure, methods of attaching the polymer to the surface of the structure having —OH functionality (e.g., $C_{alkyl}$—OH), methods of decreasing the amount of microorganisms formed on a structure, and the like, are provided herein.

18 Claims, 6 Drawing Sheets

Synthesis of linear PEI

Synthesis of sulfated quaternary PEI copolymer

¹H NMR of 2-(4-(6-bromohexyloxy) phenylsulfonyl) ethanol

¹³C NMR of 2-(4-(6-bromohexyloxy) phenylsulfonyl) ethanol

¹H NMR spectra of quaternary PEI copolymer

FTIR spectra quaternary PEI

FTIR spectra of sulfated quaternary PEI

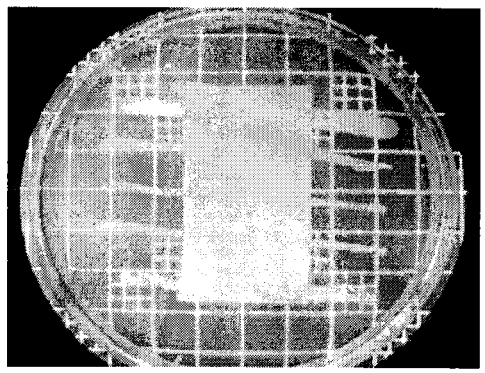
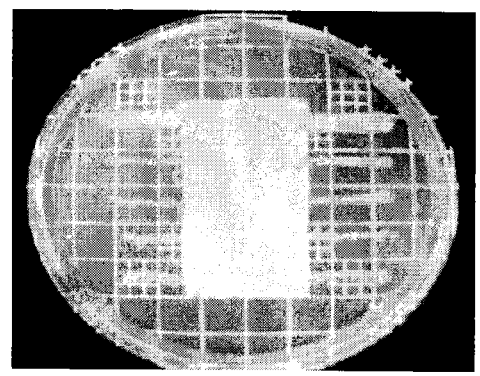
FIG. 8A and 8B
(A) Control, (B) Polymer treated fabric. The plates were streaked with *S. aureus* bacteria
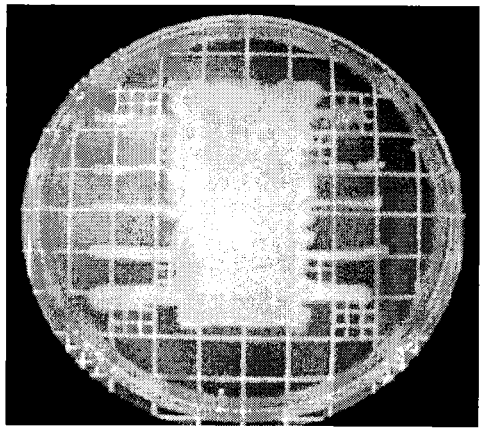
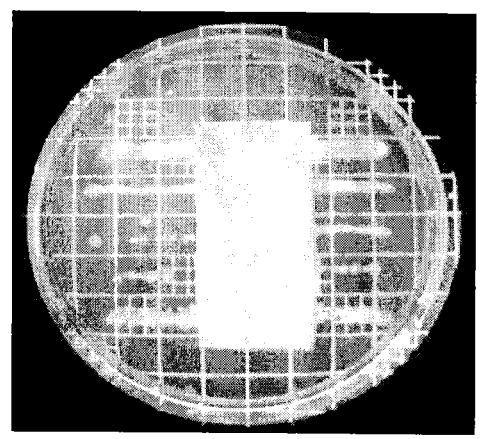
FIG. 9A and 9B
(A) Control, (B) Polymer treated fabric. The plates were streaked with *E. coli* bacteria Polymer treated fabrics after sonication (A) plate streaked with
*S. aureus* bacteria, (B) plate streaked with *E. coli* bacteria where, Y = -NH, O, S Reaction of copolymer with substrate

SYNTHESIS AND APPLICATION REACTIVE ANTIMICROBIAL COPOLYMERS FOR TEXTILE FIBERS

CROSS-REFERENCE TO RELATED APPLICATION

This application is the 35 U.S.C. §371 national stage of PCT Application No. PCT/US2012/059887, filed Oct. 12, 2012, which is herein incorporated by reference in its entirety and which also claims priority to, and the benefit of, Provisional Patent Application 61/547,120, filed Oct. 14, 2011, which is herein incorporated by reference in its entirety.

BACKGROUND

An antimicrobial agent is defined as a substance which kills or inhibits the growth of microbial cells. There are two general types of antimicrobial agents: one that kills the microbe is called a microbiocide and one that stops the growth of microbes called a microbiostat. Antimicrobial agents play a vital role in areas such as health care, hospitals, food packaging and storage, water purification, dental care, and household sanitation. Finishing with antimicrobial agents protects the user of a textile material against microbes related to aesthetic, hygienic or medical problems and protects the textile material itself against biodeterioration from mold, mildew and rot-producing fungi. Today there is substantial market for antimicrobial textiles and is increasing rapidly due to consumer awareness and demand for hygienic clothing and active-wear. In 2000, worldwide production of antimicrobial textiles was 100,000 tons and 30,000 tons in Western Europe. Production increased more than 15% a year from 2001 to 2005 in Western Europe.

There are three different means by which these finishing agents work, namely 1) controlled release mechanism, 2) the regeneration principle, and 3) the barrier or blocking action. In the first mechanism, the textile material is finished with a leachable type of antimicrobial agent which is consumed over a period of time. This type of finishing agents loses effectiveness after a few laundry washes. Another problem associated with this type of finishing agent is that microbes can develop strains that are resistant to the finish and can cause cytotoxicity. Current examples of leachable type of finishing agents are silver ions, triclosan, and polyhexamethylene biguanides (PHMB). In the regeneration principle, the finish must be reactivated by some additional step after use. For antimicrobial halamine finished fabrics the reactivation can be done with chlorine bleach. The residual chlorine odor is a problem with this finish. In the barrier mechanism, the fabric can be finished with an inert physical barrier coating material or surface coatings which can kill microbes on contact. However, present solutions have not produced satisfactory solutions, and there is a need to provide alternative solutions.

SUMMARY

Embodiments of the present disclosure, in one aspect, relate to polymer compositions, methods of making polymer compositions, structures (e.g., textile articles) having the polymer composition covalently bonded to the structure, methods of attaching the polymer to the surface of the structure having —OH functionality (e.g., $C_{alkyl}$—OH), methods of decreasing the amount of microorganisms formed on a structure, and the like.

An embodiment of the polymer, among others, includes: a sulfated quaternary polyethylenimine (PEI) copolymer represented by Structure A,

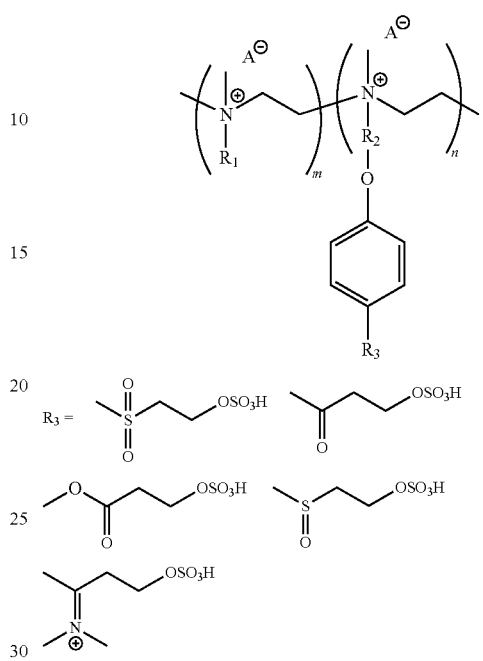

wherein R1 and R2 are each independently selected from an alkyl group, wherein A is a counter ion, and wherein m and n are each independently 1 to 25.

An embodiment of the structure, among others, includes: a sulfated quaternary polyethylenimine (PEI) copolymer represented by Structure A,

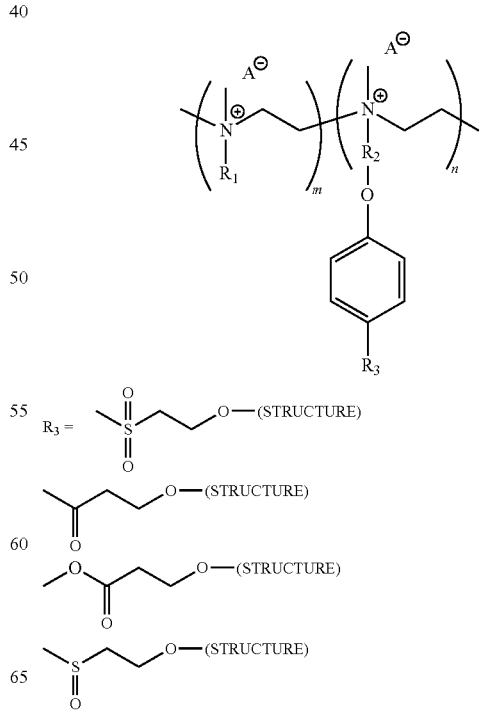

-continued

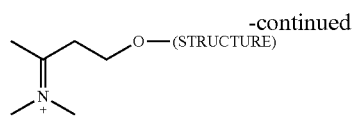

wherein R1 and R2 are each independently selected from an alkyl group, wherein A is a counter ion, wherein m and n are each independently 1 to 25, wherein the sulfated quaternary PEI copolymer is covalently attached to the structure, and wherein the structure has an antimicrobial characteristic.

An embodiment of making a polymer, among others, includes: preparing a backbone of the polymer by deacylation of poly(2-ethyl-2-oxazoline) to produce linear polyethylenimines (PEI); preparing a pendant group; and grafting the pendant group to the backbone and then quaternizing with a quaternizing compound to create a quaternary PEI having structure A:

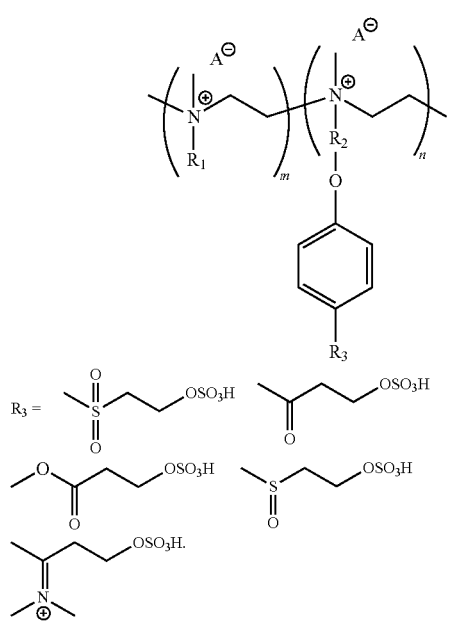

An embodiment of preparing an antibacterial textile article, among others, includes: providing a sulfated quaternary polyethylenimine (PEI) copolymer having structure A:

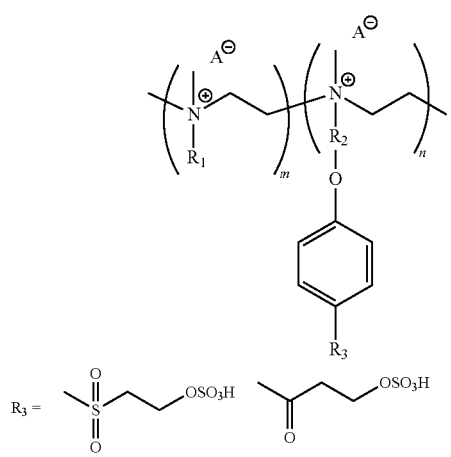

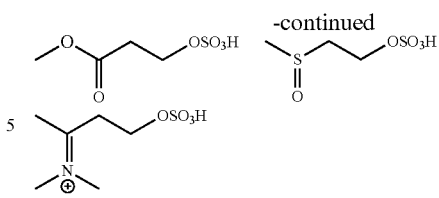

wherein R1 and R2 are each independently selected from an alkyl group, wherein A is a counter ion, and wherein m and n are each independently 1 to 25; introducing the sulfated quaternary PEI copolymer to a textile article having a group selected from $NH_2$, OH, and SH groups, while in the presence of an alkali solution; and reacting the sulfated quaternary PEI copolymer with the textile article to produce covalent bonds between the sulfated quaternary PEI copolymer and the textile article.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIGS. 8A and 8B illustrate digital images of plates streaked with *S. aureus* bacteria, where the FIG. 8A includes a control and FIG. 8B includes the sulfated quaternary PEI treated fabric.

FIGS. 9A and 9B illustrate digital images of plates streaked with *E. coli* bacteria, where FIG. 9A includes a control and FIG. 9B includes the sulfated quaternary PEI treated fabric.

DETAILED DESCRIPTION

Figure 1:
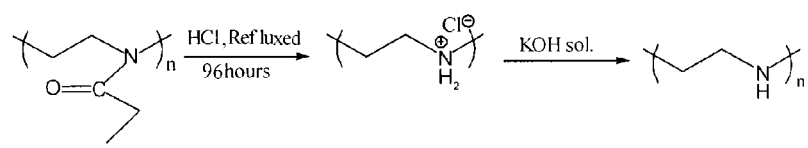
FIG. 1 illustrates a reaction scheme for the synthesis of polyethylenimine.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded, and that the substitution results in a stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon chain and a substituted saturated aliphatic hydrocarbon chain which may be straight, branched, or cyclic, having 1 to 20 carbon atoms, where the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, septyl, octyl, nonyl, decyl, and the like. The substitution can be with a halogen, for example.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

The term "substituted," as in "substituted alkyl", "substituted cycloalkyl," "substituted cycloalkenyl," substituted aryl," substituted biaryl," "substituted fused aryl" and the like, means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl group in which one or more hydrogens are substituted by halogen radicals. Examples of haloalkyl include, but are not limited to, trifluoromethyl, trichloromethyl, pentafluoroethyl, and pentachloroethyl.

The term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The term "antibacterial characteristic" refers to the ability to kill and/or inhibit the growth of bacteria. A substance having an antibacterial characteristic may be harmful to bacteria. A substance having an antibacterial characteristic can kill the bacteria and/or prevent or substantially prevent the replication or reproduction of the bacteria.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phor-* midium, *Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae.*

The term "protozoan" as used herein includes, without limitations flagellates (e.g., *Giardia lamblia*), amoeboids (e.g., *Entamoeba histolitica*), and sporozoans (e.g., *Plasmodium knowlesi*) as well as ciliates (e.g., *B. coli*). Protozoan can include, but it is not limited to, *Entamoeba coli, Entamoeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei,* and *Myxoporidia.*

The term "algae" as used herein includes, without limitations microalgae and filamentous algae such as *Anacystis nidulans, Scenedesmus* sp., *Chlamydomonas* sp., *Clorella* sp., *Dunaliella* sp., *Euglena* sp., *Prymnesium* sp., *Porphyridium* sp., *Synechoccus* sp., *Botryococcus braunii, Crypthecodinium cohnii, Cylindrotheca* sp., *Microcystis* sp., *Isochrysis* sp., *Monallanthus salina, M. minutum, Nannochloris* sp., *Nannochloropsis* sp., *Neochloris oleoabundans, Nitzschia* sp., *Phaeodactylum tricornutum, Schizochytrium* sp., *Senedesmus obliquus,* and *Tetraselmis sueica* as well as algae belonging to any of *Spirogyra, Cladophora, Vaucheria, Pithophora* and *Enteromorpha* genera.

The term "fungi" as used herein includes, without limitations, a plurality of organisms such as molds, mildews and rusts and include species in the *Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys* and *Uredinalis* genera.

As used herein, the term "fiber" refers to filamentous material that can be used in fabric and yarn as well as textile fabrication. One or more fibers can be used to produce a fabric or yarn. Fibers include, without limitation, materials such as cellulose, fibers of animal origin (e.g., alpaca, angora, wool and vicuna), hemicellulose, lignin, polyesters, polyamides, rayon, modacrylic, aramids, polyacetates, polyxanthates, acrylics and acrylonitriles, polyvinyls and functionalized derivatives, polyvinylidenes, PTFE, latex, polystyrene-butadiene, polyethylene, polyacetylene, polycarbonates, polyethers and derivatives, polyurethane-polyurea copolymers, polybenzimidazoles, silk, lyocell, carbon fibers, polyphenylene sulfides, polypropylene, polylactides, polyglycolids, cellophane, polycaprolactone, "M5" (poly{diimidazo pyridinylene(dihydroxy)phenylene}), melamine-formadehyde, plastarch, PPOs (e.g., Zylon®), polyolefins, and polyurethane.

The term "textile article" can include garments, fabrics, carpets, apparel, furniture coverings, drapes, upholstery, bedding, automotive seat covers, fishing nets, rope, articles including fibers (e.g., natural fibers, synthetic fibers, and combinations thereof), articles including yarn (e.g., natural fibers, synthetic fibers, and combinations thereof), and the like.

Discussion:

In accordance with the purpose(s) of the present disclosure, as embodied and broadly described herein, embodiments of the present disclosure, in one aspect, relate to polymer compositions, methods of making polymer compositions, structures (e.g., textile articles) having the polymer composition covalently bonded to the structure, methods of attaching the polymer to the surface of the structure having —OH functionality (e.g., $C_{alkyl}$—OH), methods of decreasing the amount of microorganisms formed on a structure, and the like. In an embodiment, the compound (or the compound disposed on a surface) has an antimicrobial characteristic (e.g., kills at least 70%, at least 80%, at least 90%, at least 95%, or at least 99% of the microorganisms (e.g., bacteria virus) and/or reduces the amount of microorganisms that form or grow on the surface by at least 70%, at least 80%, at least 90%, at least 95%, or at least 99%, as compared to a surface without the compound disposed on the surface). Additional details are described herein.

In an embodiment, the compound can be used to bind to a surface or structure of an article having O—H functionality. In an embodiment, the article can include those that are exposed to microorganisms and/or that microorganisms can grow on such as, without limitation, fibers, fabrics, textiles, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. In an embodiment, the articles may also include live biologic structures (or surfaces of live biologic structures) such as seeds for agricultural uses, tree limbs, and trunk, as well as teeth.

In an embodiment, the article inherently includes —OH groups on the surface of the structure to interact with the compound, as described below. In an embodiment, the article includes a functionalized layer disposed on the article that includes the —OH groups on the surface to interact with the compound. In an embodiment, the article can include surfaces that inherently include —OH groups on the surface of the article and also can include surfaces that include a functionalized layer disposed on the structure that includes the —OH groups. In an embodiment, the functionalized layer can have a thickness of about 2 nanometers (nm) to 1 micrometer (μm) or about 25 nm to 120 nm.

In an embodiment, the article can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures having a functionalized layer (e.g., includes a —OH group) on the surface of the structure, metals, metal alloys, or metal oxides structure having a functionalized layer (e.g., includes a —OH group) on the surface of the structure, a structure (e.g., tile, stone, ceramic, marble, granite, or the like) having a functionalized layer (e.g., includes a —OH group) on the surface of the structure, and a combination thereof.

In an embodiment, the compound is a linker that can be used to bind to surfaces or structures having $C_{alkyl}$—OH functionality such as fibers. In an embodiment, the fiber can include: a polypropylene fiber, a polyethylene fiber, a polyester fiber, a polyamide fiber, an aramid fiber, a cellulose fiber, a hemicellulose fiber, an acrylic fiber, a latex fiber, and a natural fiber, as well as natural surfaces, or another surface or structure having $C_{alkyl}$—OH functionality.

In an embodiment, the compound has a covalent bond (O—C) that forms between the compound and the surface having a —OH group or a layer on the surface having the —OH group. In other words, the compound can be attached to the surface or the layer on the surface so the bonding is easy and inexpensive to achieve. Once the covalent bond is formed, the compound layer is strongly bound to the surface and can withstand very harsh conditions such as sonication and extended washing steps as well as exposure to harsh environmental conditions (e.g., heat, cold, humidity, lake, river, and ocean conditions (e.g., above and/or under water), and the like).

As mentioned above, the compound can be disposed on a surface to produce an article that includes the compound covalently bonded to the surface of the article. In an embodiment, the method of disposing the compound on the surface of the article includes disposing the compound on the surface using a method such as spraying, dipping, spin coating, drop casting, and the like. In an embodiment, the surface of the article has —OH groups that can interact with the compound. In an embodiment, the article has a layer (also referred to as a "functionalized layer") (e.g., a thin film or self assembling layer) disposed on the surface of the structure. The functionalized layer includes —OH bonds that can interact with the compound.

After the compound is covalently bonded to the surface, the structure has an antimicrobial characteristic that is capable of killing a substantial portion of the microorganisms (e.g., bacteria, virus, or a combination of different types of microorganisms) on the surface of the article and/or inhibits or substantially inhibits the growth of the microorganisms on the surface of the article. The phrase "killing a substantial portion" includes killing at least about 70%, at least about 80%, at least about 90%, at least about 95%, or at least about 99% of the microorganism (e.g., bacteria, virus, or a combination of different types of microorganisms) on the surface that the compound is covalently bonded. The phrase "substantially inhibits the growth" includes reducing the growth of the microorganism (e.g., bacteria, virus, or a combination of different types of microorganisms) by at least about 70%, at least about 80%, at least about 90%, at least about 95%, or at least about 99% of the microorganisms on the surface that the compound is covalently bonded, relative to a structure that does not have the compound disposed thereon.

The use of polymeric antimicrobial agents for textile materials holds much promise, and involves the third mechanism mentioned above. Polymeric antimicrobial agents have the advantages of being stable, non-volatile, durable, non-permeable through the skin, non-leachable, efficient and selective. Polymeric antimicrobial agents can be designed to endow desired functional properties to the finish.

Quaternary polyethylenimines (PEIs) have unique structural properties and kill bacteria upon contact. It is hypothesized that the positive charge on the polymer interacts with the negatively charged cell wall/membrane of the bacteria, and the hydrophobic side chain on quaternary amine disrupts the cell wall/membrane causing cell lysis. The mechanism is termed as a "hole-poking" mechanism.

In an embodiment the polymer is a sulfated quaternary PEI copolymer such as that shown below. In an embodiment, R1 and R2 can independently include a substituted or unsubstituted hydrocarbon (e.g., 1 to 30 carbons) such as an alkyl, alkenyl, or an alkynyl. In an embodiment, R1 and R2 can each be independently selected from alkyl groups. In an embodiment, m and n can each be independently selected to be 1 to 25 or 3 to 25.

In an embodiment, the R1 can include a C═C group in the chain (e.g., at the terminal end). In an embodiment, the hydrophobic side chain moiety can have an alkene group attached to it so that the carbon chain includes one or more C═C bonds.

In an embodiment, R1 can have the general formula of $C_qH_{2q+1}$, where q can be 1 to 25. In an embodiment, the hydrophobic side chain (R1) can include a hydrocarbon chain such as: octane or its derivatives (e.g., 2-ethylhexane, 3-(methyl)heptane, 6-methylheptane, 2-methylheptane), decane or its derivatives (e.g., 3,7-dimethyl octane, 7-methyl nonane), dodecane or its derivatives (e.g., 4,8-dimethyl decane, 2-methyl undecane, 3-methyl undecane, 9-methyl undecane, 10-methyl undecane), tridecane or its derivatives (e.g., 2-methyl dodecane, 3-methyl dodecane, 6-methyl dodecane, 7-methyl dodecane, 8-methyl dodecane, 9-methyl dodecane, 10-methyl dodecane, 11-methyl dodecane), pentadecane or its derivatives (e.g., 3,7,11-trimethyl dodecane, 13-methyl tetradecane), hexadecane or its derivatives (e.g., 7-(methyl) pentadecane, 7-(3-propyl)tridecane), heptadecane or its derivatives (e.g., 11-methyl hexadecane, 14-methyl hexadecane, 2-methyl hexadecane), octadecane or its derivatives (e.g., 11-methyl heptadecane), nonadecane or its derivatives (e.g. 14-methyl octadecane) eicosane or its derivatives (e.g., 3,7,11,15-tetramethyl hexadecane, 9-(3-propyl) heptadecane), heneicosane or its derivatives (e.g., 20-methylheneicosane), docosane or its derivatives (e.g., 20-methyl heneicosane), tetraconsane (e.g., 11-methyl tricosane), and a combination thereof, where the combination can include a polymer that includes two or more different hydrophobic side changes. In an embodiment, one or more H groups can be substituted.

R2 can have the general formula $C_rH_{2r}$, where r can be 1 to 25. In an embodiment, R2 can be ethyl, propyl, butyl, pentyl, hexyl, heptyl, octyl, nonyl, or decyl. In an embodiment, R1 and R2 can be $C_{12}H_{25}$ and $C_6H_{12}$ groups, respectively. In an embodiment, one or more H groups can be substituted.

The counter anion, A, on quaternary amine polymer can include anions such as chloride, bromide, iodide, alkyl sulfate anions (e.g., methyl sulfate, ethyl sulfate, dodecylsulfate), tetrafluoroborate, tosylate, sulfate, chlorate, or a combination thereof. In an embodiment, the counter anion is iodide.

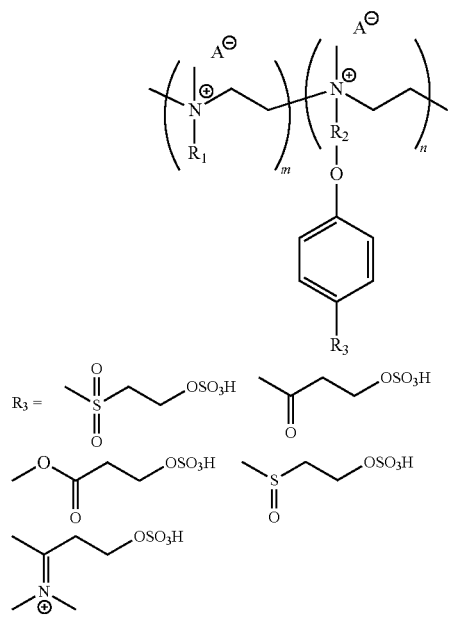

Figure 2:
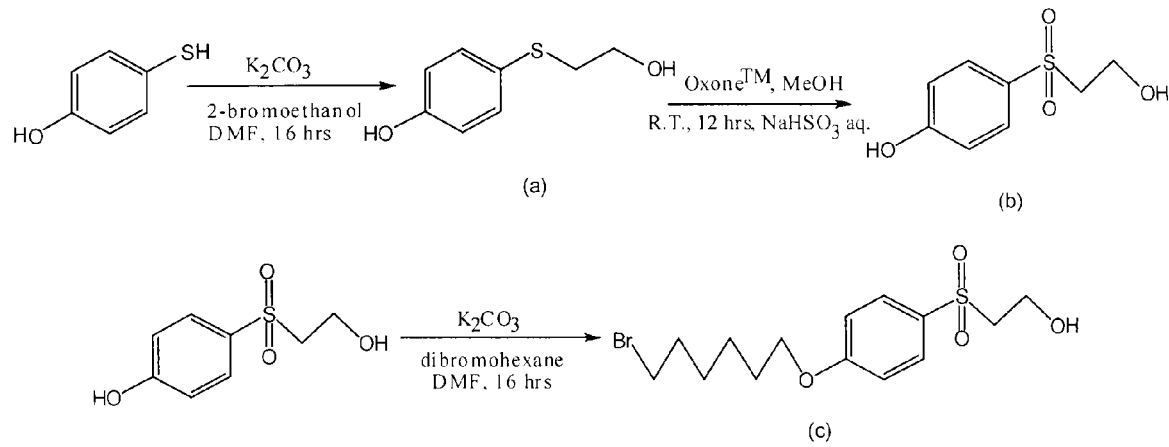
FIG. 2 illustrates a reaction scheme for the synthesis of a pendant group.

In an embodiment, the sulfated quaternary PEI copolymer can be prepared by preparing a backbone of the polymer by deacylation of poly(2-ethyl-2-oxazoline) to produce linear polyethylenimines (PEI). Then a pendant group is prepared (e.g., the process in FIG. 2). The pendant group is grafted to the backbone and then quaternized with quaternizing compound (e.g., iodomethane, dimethyl sulfate, benzyl chloride, and methyl tosylate) to create a quaternary PEI.

In an embodiment, the pendant group can be prepared by treating bromoethanol with mercaptophenol to obtain 4-(2-hydroxyethylsulfanyl) phenol. Then the obtained product is reacted with $2KHSO_5 \cdot KHSO_4 \cdot K_2SO_4$ to yield 4-(2-hydroxyethansulfonyl) phenol. Subsequently, the obtained intermediate is reacted with dibromohexane to yield 2-(4-(6-bromohexyloxy)phenylsulfonyl) ethanol to yield the pendant group. Alternatively, dibromohexane can be replaced with dibromoethane, 1,3-dibromopropane, 1,4-dibromobutane, 1,5-dibromopentane, 1,7-dibromoheptane, 1,8-dibromooctane, 1,9-dibromononane, and 1,10-dibromodecane. In an embodiment, the pendant group has one bromo end group that can react with linear PEI and the hydroxy end of the pendant group is modified to generate a fiber reactive crosslinker.

Figure 11:
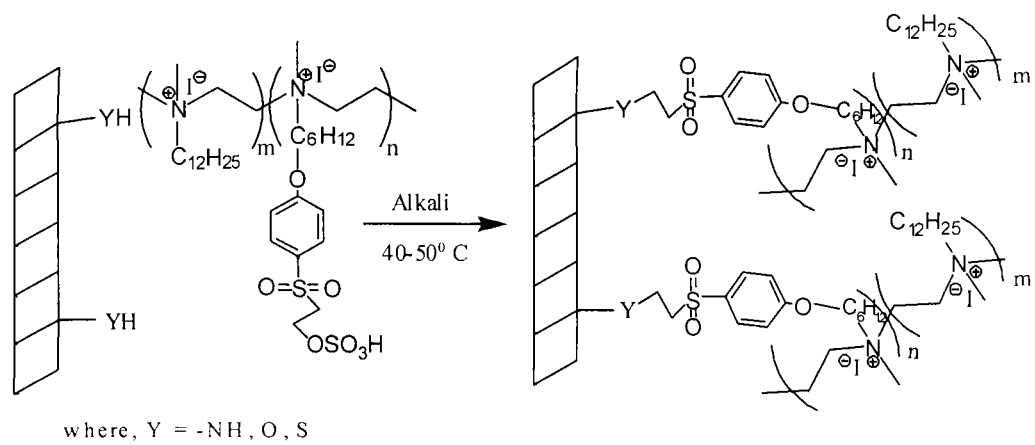
FIG. 11 illustrates a reaction scheme of the sulfated quaternary PEI reacted with a fabric.

In addition, embodiments of the present disclosure can include the sulfated quaternary PEI copolymer covalent bonded to a textile article (e.g., See FIG. 11). In an embodiment, the structure can include textile articles, fibers, filters or filtration units (e.g., HEPA for air and water), and the like. Additional details are described in Example 1.

In general, the sulfated quaternary PEI copolymer is introduced to a textile article having $NH_2$, OH, and/or SH groups in the presence of alkali solution (e.g., pH 8-12, dissolved in water) at a temperature of about 30 to 60° C. or 40 to 95° C. The sulfated quaternary PEI copolymer is covalently bonded to the NH, O, or S group on the textile article while $H_2SO_4$ is removed. The textile article having the covalently bonded sulfated quaternary PEI copolymer is advantageous since the textile article has antibacterial activity and retains the antibacterial activity for an extended period of time (e.g. days to week, to months, or to years).

In an embodiment, the compound can be attached to a structure, where R3 is in the following manner:

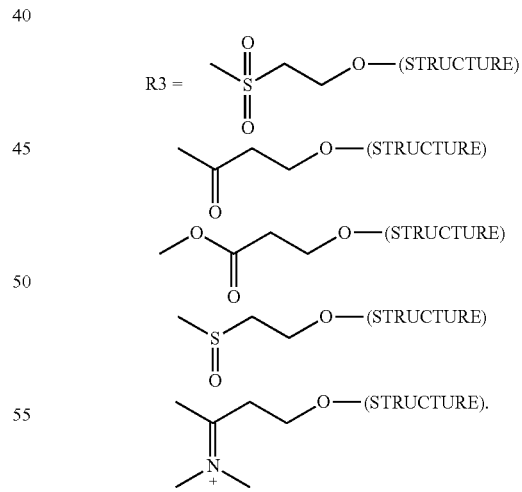

EXAMPLES

Now having described the embodiments of the present disclosure, in general, Example 1 describes some additional embodiments of the present disclosure. While embodiments of present disclosure are described in connection with Example 1 and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Embodiments of the present disclosure include the design of novel reactive polymeric antimicrobial finishing agent for application to textile materials using an existing simple application method such as the exhaust method. The chemicals which have an affinity towards textile fibers are applied through exhaustion process in dyeing machines. In textile industry, most of the chemical finishing processes are water based where water acts as a relatively cheap and safe solvent. The use of organic solvents is very limited in textile industry because of cost, flammability, toxicity and hazardous nature of most of the solvents [8].

The synthesized copolymer is ionic in nature with affinity towards textile fibers and dispersibility in water. The vinyl sulfone based reactive group on the polymer backbone can react with fiber to form a covalent linkage under appropriate pH and temperature conditions. The vinyl sulfone group can react with nucleophiles like thiols, amines, nitriles [9], and alcohols. The covalent attachment of active quaternary PEI will render the finish durable.

Materials:

The following chemicals were used as received in the synthesis and antibacterial testing: Poly(2-ethyl-2-oxazoline) (Aldrich), tert-amylalcohol (Aldrich), dimethylsulfoxide (DMSO) (Aldrich), 4-hydroxythiophenol (TCI America), 2-bromoethanol (Alfa Aesar), Oxone™ ($2KHSO_5.KHSO_4.K_2SO_4$) (Alfa Aesar), 1-bromododecane (Alfa Aesar), Iodomethane (Alfa Aesar), 1,6 dibromohexane (Alfa Aesar), Nutrient agar (NA) (Difco™), and Nutrient Broth (NB) (Difco™). The desized and bleached, 100% cotton print cloth was purchased from Testfabric.inc, West Pittston, Pa. with specification of (weave 78×76, weight 102 $g/m^2$) as a test fabric. The fabric was further cleaned by treatment with boiling water for 30 mins and oven dried. Gram positive and Gram negative bacteria namely, S. aureus (ATCC 6538) and E. coli (obtained from UGA dept of microbiology) were used in antibacterial testing.

Instrumental Methods:

The synthesized compounds were analyzed using proton ($^1H$) and carbon ($^{13}C$) Nuclear Magnetic Resonance (NMR) spectroscopy and spectra were recorded using a Varian Mercury 300 NMR spectrometer working at 300 MHz. An internal standard of tetramethylsilane is used to report relative chemical shifts. Fourier Transform Infrared (FTIR) measurements were taken with a Nicolet model 6700 instrument at 128 scans with 4 $cm^{-1}$ resolution for analysis of compounds. The compound was thoroughly mixed and crushed with dry potassium bromide (KBr). A transparent pellet of mixture was made by using Beckman pelletizer to take FTIR spectra.

Syntheses:

Linear Polyethylenimine (PEI): The deacylation reaction was performed according to a literature procedure (*PNAS*, 2005, 102, 5679) [10] (FIG. 1). Three grams of the poly(2-ethyl-2-oxazoline, $M_w$, 50 kDa) (POEZ) was added to 120 mL of 24% (w/v) HCl, followed by refluxing for 96 hours. The POEZ crystal dissolved completely in 1 hour, but a white precipitate appeared after 3 hours of refluxing. The precipitate was filtered and then air-dried. The protonated polymer was dissolved in water and neutralized with KOH solution and isolated by filtration. The white powder was isolated by filtration, washed with distilled water until the pH became neutral, and dried under vacuum. The yield of the reaction was 1.15 g (88%). The product was confirmed by proton NMR spectroscopy and the peak values are $^1H$ NMR ($CDCl_3$): δ, 2.72 (s, 4H, $NCH_2CH_2N$), 1.71 (1H, NH).

4-(2-hydroxyethylsulfanyl)phenol: (FIG. 2) (a) (4-(2-hydroxyethylsulfanyl) phenol) was synthesized by a modified literature procedure (pl add ref). 4-hydroxythiophenol (mercaptophenol) (6.00 g, 47.61 mmole), 2-bromoethanol (5.90 g, 47.6 mmol) and $K_2CO_3$ (6.6 g, 47.48 mmol) was stirred in dimethylformamide (DMF, 50 ml) at −5° C. for 30 minutes. The reaction mixture was then stirred for 12 hours at room temperature. The reaction mixture was poured in ice water (300 ml) and extracted with dichloromethane (DCM) (3×50 ml). The organic part was dried by $MgSO_4$ and then solvent was removed under a rotary evaporator. The crude product was purified on silica gel column by using a chloroform/methanol (94:6) solvent mixture. Yield: 72%. $^1H$ NMR ($CDCl_3$): δ, 8.01 (s, OH, 1H), 7.33 (d, 2H, J=8.7 Hz), 6.78 (d, 2H, J=8.7 Hz), 4.52 (s, OH, 1H), 3.67 (t, 2H, J=6 Hz), 2.99 (t, 2H, J=5.7).

4-(2-hydroxyethansulfonyl)phenol: In the next step, the reaction was carried out according to a literature procedure (*Organic Process Research & Development*, vol 7, No. 3, 2003) [11] in which 4-(2-hydroxyethylsulfanyl) phenol (5.85 g, 34.41 mmole) in methanol was stirred with Oxone™ ($2KHSO_5.KHSO_4.K_2SO_4$) (30.24 g) at 10° C. for 20 minutes and then at room temperature for 12 hours. The reaction mixture was filtered, 1 ml of 38-40% aqueous $NaHSO_3$ solution was added, and the pH adjusted to 7 using aqueous NaOH (28%) solution. The mixture was again filtered and the solvent removed by rotary evaporator. The crude product was purified on a silica gel column using DCM/methanol (91:9) solvent mixture. Solvent was removed by rotary evaporator to yield (75%) a solid white product. $^1H$ NMR (DMSO-$d_6$): δ, 10.56 (s, OH, 1H), 7.67 (d, 2H, J=7.8), 6.9 (d, 2H, J=7.5), 3.62 (t, 2H, J=6.9), 3.31 (t, 2H, J=6.6).

2-(4-(6-bromohexyloxy)phenylsulfonyl)ethanol: The intermediate (b) (5.22 g, 30.70 mmole) was then stirred with dibromohexane (31.52 g, 130.24 mmole) to create the intermediate (c). The reaction was carried out at room temperature for 16 hours under nitrogen atmosphere in DMF (70 ml) solvent in the presence of $K_2CO_3$ (4.3 g, 30.8 mmol). The reaction mixture was poured in ice water (300 ml) and extracted with DCM (3×50 mL). The organic part was dried with $MgSO_4$ and the solvent was removed by rotary evaporator. The crude product was purified on silica gel column using a DCM/methanol (95:5) solvent mixture. Yield: 54.25%. $^1H$ NMR ($CDCl_3$): δ, 7.84 (d, 2H, J=9 Hz), 7.06 (d, 2H, J=9 Hz), 4.04 (t, 2H, J=6 Hz), 3.98 (t, 2H, J=6.9 Hz), 3.43 (t, 2H, J=6.9 Hz), 3.32 (t, 2H, J=3.6 Hz), 1.9-1.7 (m, 4H), 1.6-1.4 (m, 4H). $^{13}C$ NMR ($CDCl_3$): δ, 163.76, 130.39, 115.26, 68.56, 58.69, 56.72, 33.89, 32.77, 31.13, 29.00, 28.02.

Figure 3:
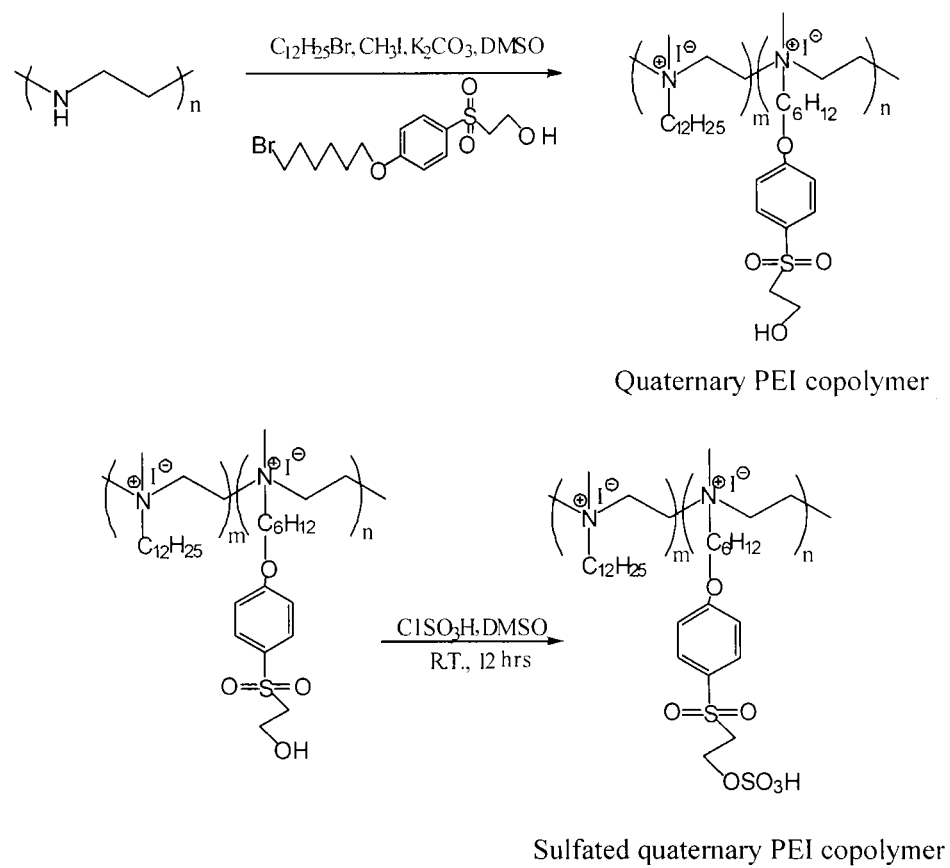
FIG. 3 illustrates a reaction scheme for the synthesis of a sulfated quaternary PEI copolymer.
Figure 4:
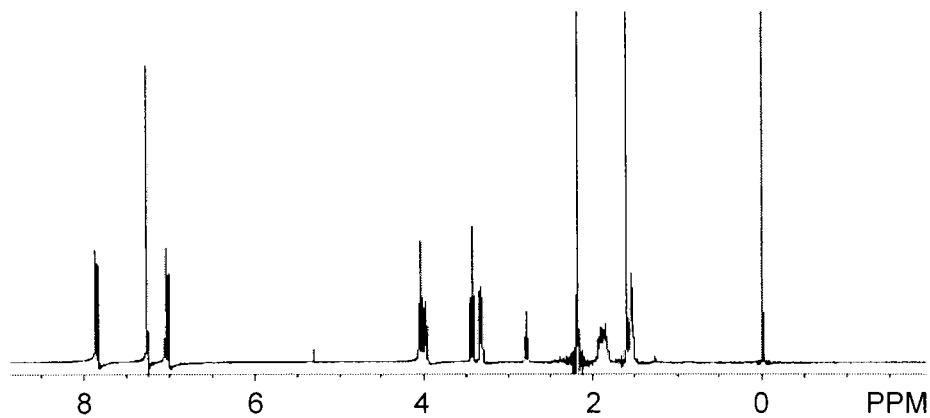
FIG. 4 illustrates a $^1H$ NMR spectrum of 2-(4-(6-bromohexyloxy)phenylsulfonyl) ethanol.
Figure 5:
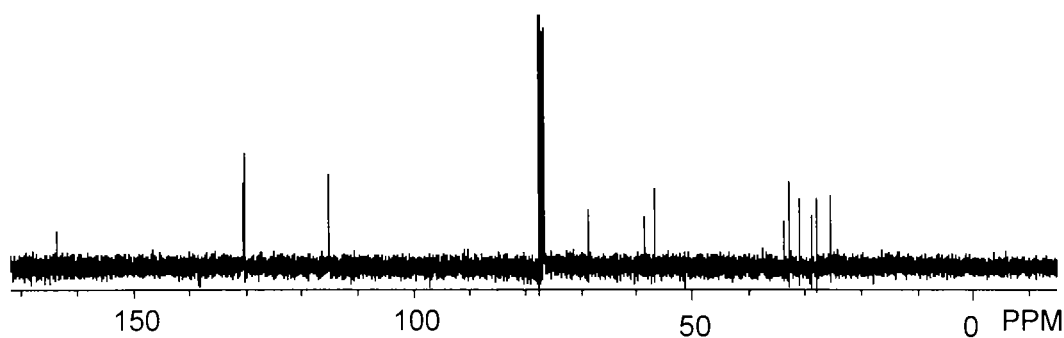
FIG. 5 illustrates a $^{13}C$ NMR spectrum 2-(4-(6-bromohexyloxy)phenylsulfonyl) ethanol.
Figure 6:
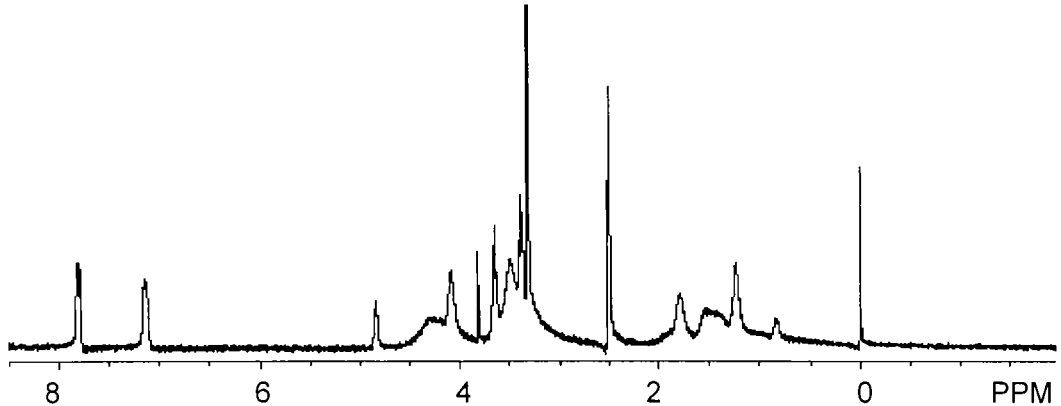
FIG. 6 illustrates a $^1H$ NMR spectrum of quaternary PEI copolymer.

Quaternary PEI Copolymer: (FIG. 3) The intermediate (c) (2.55 g, 7 mmol) and 1-bromododecane (1.8 g, 7 mmol) and $K_2CO_3$ (2.10 g, 15 mmol) were stirred with deacylated PEI (0.6 g, 13.95 mmole) intermediate at 95° C. for 96 hours in 50 ml of DMSO solvent. The reaction mixture was filtered and $CH_3I$ (2.94 g, 20.92 mmole) was added to the filtrate. The mixture was stirred at 60° C. for 24 hours, cooled at room temperature and then excess chloroform was added to precipitate quaternized PEI copolymer with 48% yield. (e). $^1H$ NMR (DMSO): δ, 7.8 (bs, 2H), 7.13 (bs, 2H), 3.65-3.32 (m, 22H), 1.8-0.7 (m, 31H).

Sulfated Quaternary PEI Copolymer (SQ-PEI): The chlorosulfonic (0.10 g, 0.89 mmol) and pyridine (0.035 g, 0.45 mmol) was added to the solution of copolymer (0.7 gg, 0.89 mmole) in DMSO (20 ml). The mixture was stirred for 12 hours at room temperature. The copolymer was precipitated from reaction mixture by adding excess chloroform. The precipitate was filtered and washed with water and later with chloroform. The product was then dried in vacuum. Yield: 51%. Pl add IR data.

Antimicrobial Test:

The treated fabrics were tested by AATCC Test Method 147-2003: Antibacterial Activity Assessment of Textile Materials: Parallel Streak Method, which is a preliminary screening and qualitative test. The test was carried out using *S. aureus* and *E. coli* representing Gram positive and Gram negative bacteria, respectively. Bacteria are classified into Gram positive or Gram negative categories based on the reaction of bacteria to the Gram stain test. Gram stain result depends on the bacterial cell wall structure. The Gram positive bacterial cell wall consists of plasma membrane, periplasmic space and thick layer of peptidoglycan. The Gram negative bacterial cell wall is more complex and is made up of plasma membrane, periplasmic space, and a thin layer of peptidoglycan. The outer layer consists of lipopolysaccharide and protein. Because of the different cell wall structures the bacteria have different defense mechanisms and therefore it is important to assess the efficacy of antibacterial agent against both types of bacteria to confirm broad range activity.

Three replications were done for each treatment. The bacteria were incubated in a nutrient broth for 24 hours at 37° C. The bacterial solution was diluted 10 fold and the diluted inoculum was used for making parallel streaks across nutrient agar plates. Five parallel streaks of approximately 60 mm length were made on each agar plate with approximately 10 mm spacing between the streaks. The fabric specimen (2.5×5 cm) was kept in intimate contact with the inoculum streaked agar. The agar plates were incubated for 24 hours at 37° C. in an incubator before taking pictures.

Finishing of Fabric:

The new copolymer was applied by exhaust method to cotton fabric. The copolymer was added to water and stirred to create a dispersion. The bleached cotton fabric (5×5 cm) was treated with finishing solution for 20-30 min at 45-50° C. The pH of the finishing solution was then adjusted to 9-10 by adding NaOH solution. The treatment was continued for 30-40 minutes at 45-50° C. The fabric was rinsed thoroughly with water after the application process and dried in air. The fabric was treated with a 2% finish on weight of fabric (owf) with a material to liquor ratio of 1:40. The treated fabric was cut into two halves and one half was sonicated for 5 minutes to remove physically absorbed finish.

Results and Discussion

Syntheses:

The new copolymer was synthesized in two parts. First, the backbone of the polymer was synthesized by deacylation of poly(2-ethyl-2-oxazoline) to get linear polyethylenimines (PEI). In the second part the pendant group was synthesized in a series of steps. The mercaptophenol was treated with bromoethanol to obtain 4-(2-hydroxyethylsulfanyl) phenol. The obtained product was then reacted with 2KHSO$_5$.KHSO$_4$.K$_2$SO$_4$(Oxone™) which is a commercially available oxidizing agent to yield 4-(2-hydroxyethansulfonyl) phenol. The obtained intermediate was then finally reacted with dibromohexane to yield 2-(4-(6-bromohexyloxy)phenylsulfonyl) ethanol which we use as pendant group in the final polymer. The synthesized pendant group has one bromo end group which can react with linear PEI and the hydroxy end of the pendant group can be modified to generate fiber reactive crosslinker. The obtained pendant group and bromododecane (50:50) were grafted onto linear PEI. The obtained copolymer was quaternized with iodomethane to create a quaternary PEI. The quaternary PEI was then sulfated with chlorosulfonic acid to obtain the final product which under appropriate application conditions can react with the fiber.

The syntheses of all the compounds were confirmed by NMR and FTIR spectroscopy. The compounds and intermediates were successfully synthesized with moderate to high yield. FIGS. 4, 5, 6 and 7 show proton and carbon NMR of 2-(4-(6-bromohexyloxy)phenylsulfonyl) ethanol and quaternary PEI. Currently, optimization of reaction conditions is being done to improve yield of quaternary PEI and SQ-PEI compounds.

Figure 7A:
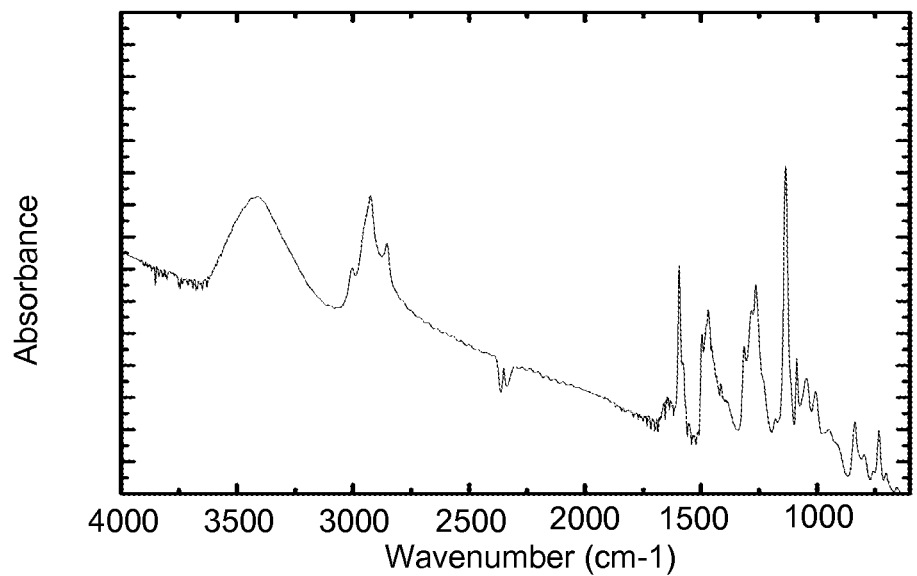
FIG. 7A illustrates an FTIR spectrum of quaternary PEI.
Figure 7B:
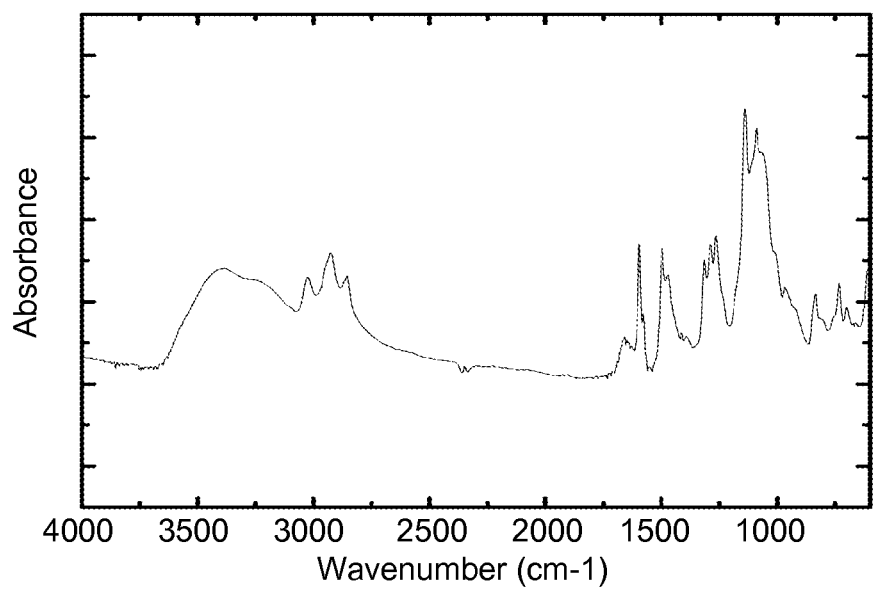
FIG. 7B illustrates an FTIR spectrum of sulfated quaternary PEI.

The final copolymer is sparingly soluble in standard NMR solvents like CDCl$_3$, DMSO-d$_6$, and D$_2$O and therefore the product was confirmed by FTIR spectra. The FTIR spectra of quaternized PEI and sulfated quaternary PEI exactly matches peak by peak except there are additional peaks around ~1000-1090 cm$^{-1}$ for S—O—C stretching vibrations after introducing sulfate group on the polymer. The bands around 1400 and 1200 cm$^{-1}$ are attributed to asymmetric and symmetric stretching vibrations of sulfone groups (—SO$_2$—) in the polymer (FIG. 7).

Figures 10A, 10B:
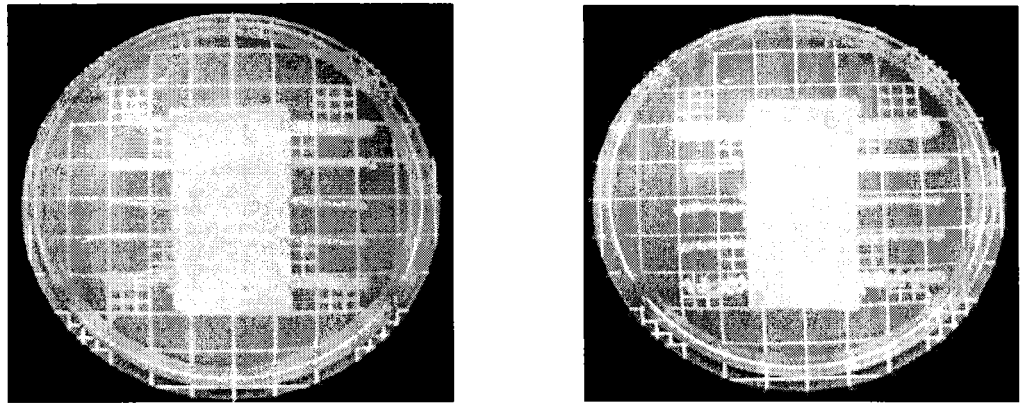
FIGS. 10A and 10B illustrate digital images of plates streaked with *S. aureus* bacteria and *E. coli* bacteria, respectively.

Microbiological Testing:

The qualitative analysis was confirmed by the AATCC 147 test, which shows that the polymer works as an effective antibacterial agent. There is no zone of inhibition around the fabric, but the finish effectively kills all the bacteria which come in contact with fabric, and there are no bacterial colonies under the finished fabric. The results suggest that the polymer does not leach out from finished fabric (FIGS. 8 and 9). The treated fabric shows the same effectiveness after harsh sonication treatments (FIG. 10) indicating that the copolymer forms a covalent bond with the cellulose. It is also observed that the finishing agent is effective against both *S. aureus* and *E. coli*, which are Gram positive and Gram negative bacteria, respectively. This indicates that the finishing agent can be effective against a broad range of bacteria.

Application on Substrate:

The Sulfated quaternary polyethylenimine (SQ-PEI) copolymer forms a dispersion in water at a neutral pH and dissolves completely in water at alkaline pH due to salt formation at sulfated group. The polymer is expected to undergo Michael addition reaction to form a covalent bond with substrate under alkaline conditions at 40-50° C. The vinyl group generated under alkaline conditions can react with the nucleophile of substrate to form a covalent bond. The covalent attachment of copolymer to fiber will render durability to the finish. The general reaction schematic of polymer with substrate is shown in FIG. 11.

Conclusion

Embodiments of the copolymer have very promising initial results and have the potential to be incorporated in current production lines of textile processing. There was no change in the visual or physical appearance of the fabric finished with sulfated quaternary polyethylenimine (SQ-PEI). The SQ-PEI finished cotton fabric showed antibacterial activity against both *S. aureus* and *E. coli*, Gram positive and Gram negative bacteria, respectively. The finished fabric showed antibacterial activity even after sonication.

References, each of which is incorporated herein by reference
1. Patrick, G. L., *An Introduction to Medicinal Chemistry*. Oxford University Press: 1995; pp 336
2. Mitesh B. Patel, S. A. P., Arabinda Ray, Rajni M. Patel, *Journal of Applied Polymer Science*, Vol. 89, 2003, pp 895-900

3. Yuan G. Robin c. *Textile Research Journal*, Vol 78 (1), 2009, pp 60-72
4. Lichter J., Vliet K., and Rubner M., *Macromolecules*, Vol 42, 2009, pp 8573-8586.
5. Bajaj, P., *Journal of Applied Polymer Science*, Vol. 83, 2002, pp 631-659.
6. El-Refaie Kenawy, S. D. W., Roy Broughton, *Biomacromolecules* Vol. 8, No. 5, 2007, pp 1359-1384.
7. Lin J, S. Q., Kim Lewis, Alexander Klibanov, *Biotechnology and Bioengineering* Vol 83, 2003, (2), pp 168-172
8. Schindler W. D., Hauser P. J., '*Chemical Finishing of Textiles*', Woodhead Publishing in Textiles: 2000; pp 7.
9. Meadows Christopher D., Gervay-Hague J., *Medicinal Research Reviews*, Vol. 26, No. 6, 2006 pp 793-814.
10. Mini Thomas, James J. Lu, Qing Ge, Chengcheng Zhang, Jianzhu Chen, and Klibanov A. M., *PNAS*, Vol 102, 2005, (16), pp 5679-5684.
11. Scalone M., Waldmeier P., *Organic Process Research & Devolpment*, Vol. 7, 2003, (3), pp 418-425.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the numerical value and measurement technique. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Therefore, at least the following is claimed:

1. A polymer comprising:
    a sulfated quaternary polyethylenimine (PEI) copolymer represented by Structure A,

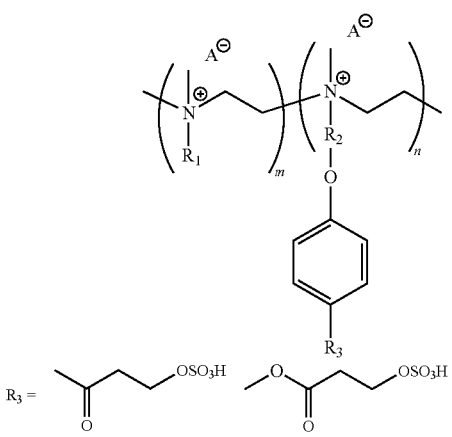

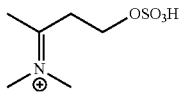

wherein R1 and R2 are each independently selected from an alkyl group, wherein A is a counter ion, and wherein m and n are each independently 1 to 25.

2. The polymer of claim 1, wherein R1 has the formula of $C_qH_{2q+1}$, where q is 1 to 25, and R2 has the formula $C_rH_{2r}$, where r is 1 to 25.

3. The polymer of claim 1, wherein the A is selected from the group consisting of: chloride, bromide, iodide, an alkyl sulfate anion, tetrafluoroborate, tosylate, sulfate, chlorate, and a combination thereof.

4. A structure, comprising:
    a sulfated quaternary polyethylenimine (PEI) copolymer represented by Structure A,

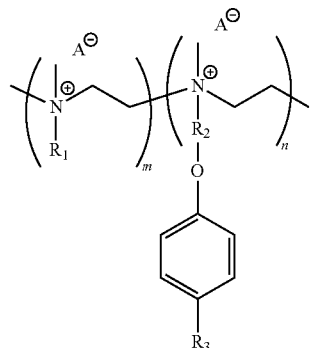

wherein R1 and R2 are each independently selected from an alkyl group, wherein A is a counter ion, wherein m and n are each independently 1 to 25, wherein the sulfated quaternary PEI copolymer is covalently attached to the structure, and wherein the structure has an antimicrobial characteristic.

5. The structure of claim 4, wherein the structure is selected from the group consisting of:
    a fabric, a textile article, a natural fiber, a synthetic fiber, a porous membrane, and a combination thereof.

6. The structure of claim 4, wherein R1 has the formula of $C_qH_{2q+1}$, where q is 1 to 25, and R2 has the formula $C_rH_{2r}$, where r is 1 to 25, and wherein the A is selected from the group consisting of: chloride, bromide, iodide, an alkyl sulfate anion, tetrafluoroborate, tosylate, sulfate, chlorate, and a combination thereof.

7. A method of making a polymer, comprising:
    preparing a backbone of the polymer by deacylation of poly (2-ethyl-2-oxazoline) to produce linear polyethylenimines (PEI);
    preparing a pendant group; and
    grafting the pendant group to the backbone and then quaternizing with a quaternizing compound to create a quaternary PEI having structure A:

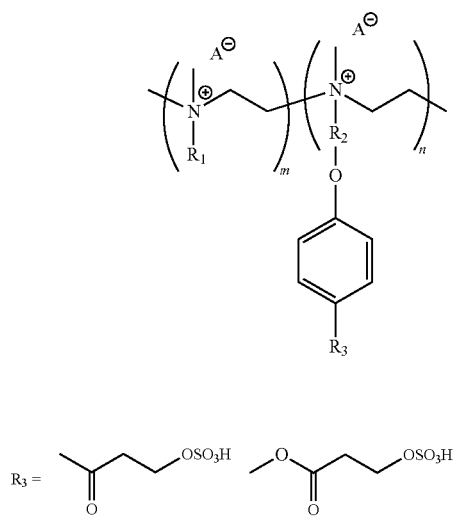

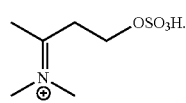

wherein R1 and R2 are each independently selected from an alkyl group, wherein A is a counter ion, and wherein m and n are each independently 1 to 25.

8. The method of claim 7, wherein preparing the pendant group includes:
   treating bromoethanol with mercaptophenol to obtain 4-(2-hydroxyethylsulfanyl) phenol;
   reacting the obtained product with 2KHSO$_5$·KHSO$_4$·K$_2$SO$_4$ to yield 4-(2-hydroxyethansulfonyl) phenol; and
   reacting the obtained intermediate with dibromohexane to yield 2-(4-(6-bromohexyloxy) phenylsulfonyl) ethanol to yield the pendant group.

9. The method of claim 8, wherein the pendant group has one bromo end group which reacts with linear PEI and the hydroxy end of the pendant group is modified to generate a fiber reactive crosslinker.

10. The method of claim 4, wherein quaternizing compound is iodomethane.

11. A method of preparing an antibacterial textile article, comprising:
    providing a sulfated quaternary polyethylenimine (PEI) copolymer having structure A:

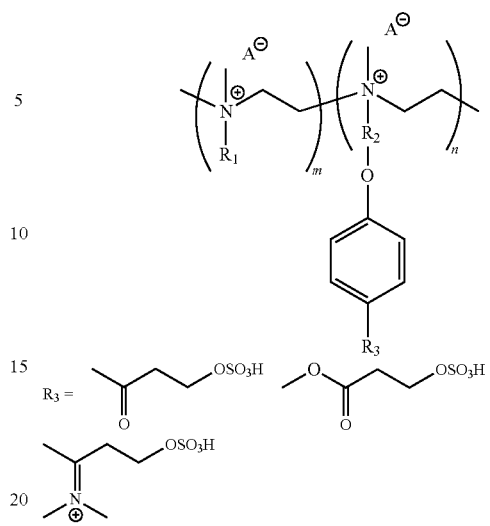

wherein R1 and R2 are each independently selected from an alkyl group, wherein A is a counter ion, and wherein m and n are each independently 1 to 25;
    introducing the sulfated quaternary PEI copolymer to a textile article having a group selected from NH$_2$, OH, and SH groups, while in the presence of an alkali solution; and
    reacting the sulfated quaternary PEI copolymer with the textile article to produce covalent bonds between the sulfated quaternary PEI copolymer and the textile article.

12. The method of claim 11, wherein the structure is selected from the group consisting of:
    a fabric, a textile article, a natural fiber, a synthetic fiber, a porous membrane, and a combination thereof.

13. The method of claim 11, wherein R1 has the formula of C$_q$H$_{2q+1}$, where q is 1 to 25, and R2 has the formula C$_r$H$_{2r}$, where r is 1 to 25.

14. The method of claim 11, wherein the A is selected from the group consisting of: chloride, bromide, iodide, an alkyl sulfate anion, tetrafluoroborate, tosylate, sulfate, chlorate, and a combination thereof.

15. An antibacterial textile article prepared according to claim 11.

16. A structure comprising, a deprotonated derivative of the polymer of claim 1 covalently bound to polysaccharide.

17. The structure of claim 16, where the polysaccharide is cellulose.

18. The structure of claim 16, where the polysaccharide is hemicellulose.

* * * * *